United States Patent [19]

Kaneshiki et al.

[11] Patent Number: 4,777,306
[45] Date of Patent: Oct. 11, 1988

[54] METHOD FOR SELECTIVE SEPARATION OF 2,6-DICHLOROTOLUENE

[75] Inventors: Toshitaka Kaneshiki; Tadayoshi Haneda; Makoto Suzuki; Yuichi Hane, all of Koriyama, Japan

[73] Assignee: Hodogaya Chemical Co., Ltd., Tokyo, Japan

[21] Appl. No.: 62,385

[22] Filed: Jun. 15, 1987

Related U.S. Application Data

[63] Continuation of Ser. No. 844,612, Mar. 27, 1986, abandoned.

[30] Foreign Application Priority Data

Apr. 15, 1985 [JP] Japan .................................. 60-78445

[51] Int. Cl.<sup>4</sup> ....................... C07C 17/38; C07C 25/00
[52] U.S. Cl. .................................................. 570/211
[58] Field of Search ........................................ 570/211

[56] References Cited

U.S. PATENT DOCUMENTS

| 2,958,708 | 11/1960 | Fleck et al. | 570/211 |
| 4,254,062 | 3/1981 | Wambach et al. | 570/211 |
| 4,453,029 | 6/1984 | Dessau | 585/820 |

FOREIGN PATENT DOCUMENTS

| 0199212 | 10/1986 | European Pat. Off. | 570/211 |
| 2166734 | 5/1986 | United Kingdom | 570/211 |

Primary Examiner—Werren B. Lone
Attorney, Agent, or Firm—Oblon, Fisher, Spivak, McClelland & Maier

[57] ABSTRACT

A method for selective separation of 2,6-dichlorotoluene from a mixture of dichlorotoluene isomers by means of a zeolite-type adsorbent, wherein ZSM-5 type zeolite is used as the adsorbent for selectively separating 2,6-dichlorotoluene as a non-adsorbed component.

3 Claims, 1 Drawing Sheet

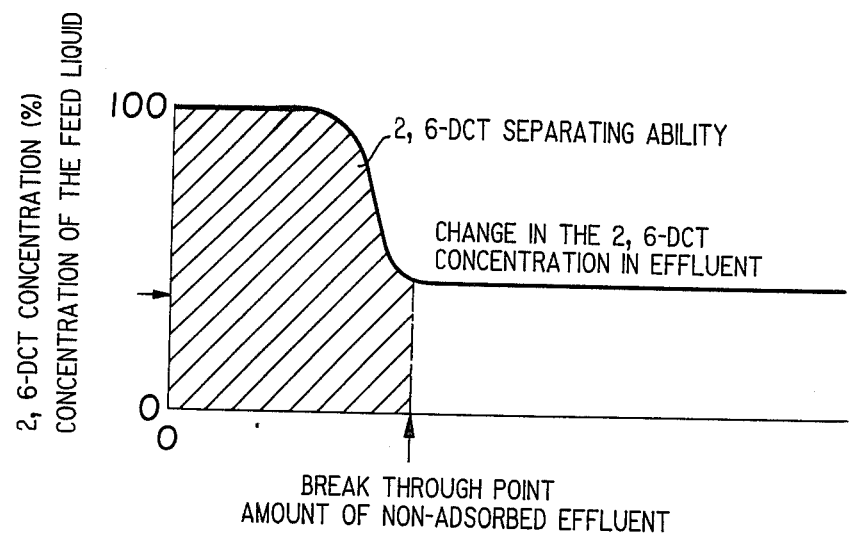

METHOD FOR SELECTIVE SEPARATION OF 2,6-DICHLOROTOLUENE

This application is a continuation of application Ser. No. 844,612, filed on Mar. 27, 1986, now abandoned.

The present invention relates to a method for selective separation of 2,6-dichlorotoluene from a mixture of dichlorotoluene (hereinafter referred to simply as "DCT") isomers. The present invention provides an adsorbent for a method for selectively separating 2,6-DCT in high purity from a mixture of DCT isomers.

2,6-DCT is an important intermediate for the production of agricultural chemicals, medicines or dyestuffs.

A mixture of DCT isomers is obtainable by chlorination of toluene or a monochlorotoluene. However, the boiling points of the respective isomers are extremely close to one another, and it is very difficult to separate 2,6-DCT by rectification. Under these circumstances, 2,6-DCT is produced in an industrial scale by dichlorination of p-toluene sulfonic acid, followed by desulfonation.

Further, U.S. Pat. No. 4,254,062 and Japanese Unexamined Patent Publication No. 199642/1984 disclose a method for adsorbing and separating 2,6-DCT from a mixture of DCT isomers by using faujasite type zeolite However, in the method for the production from p-toluene sulfonic acid, it is difficult to obtain 2,6-DCT in high purity. Besides, the method is not economical one. On the other hand, in the latter technique for the adsorption and separation by means of the zeolite, 2,6-DCT is separated and recovered from a mixture of DTC isomers as an extract component. However, the adsorption by the faujasite type zeolite is not adequate, and it is practically difficult to separate and obtain 2,6-DCT in high purity, or it is impossible to separate and recover it unless the adsorption and separation are conducted in the presence of a benzene-substituted compound.

Under these circumstances, the present inventors have conducted extensive researches on a method for effectively adsorbing, separating and recovering 2,6-DCT in high purity from a mixture of DCT isomers, and have found a peculiar catalyst which is, surprisingly, capable of selectively separating 2,6-DCT as a non-adsorbed component. The present invention has been accomplished on the basis of this discovery.

Namely, the present invention provides a method for selective separation of 2,6-DCT from a mixture of DCT isomers by means of a zeolite-type adsorbent, wherein ZSM-5 type zeolite is used as the adsorbent for selectively separating 2,6-DCT as a non-adsorbed component.

Now, the present invention will be described in detail with reference to the preferred embodiments. Referring to the accompanying drawing, FIG. 1 is a break through curve of the adsorbent showing the amount of 2,6-DCT effluent till ZSM-5 type zeolite reaches the break through point when a mixture of DCT isomers is subjected to the adsorption and separation by means of ZSM-5.

ZSM-5 type zeolite used in the present invention is an adsorbent having extremely peculiar characteristics such that it does not adsorb a 1,2,3-trisubstituted benzene represented by 2,6-DCT intended by the present invention, while it shows strong adsorption of a 1,2,4-trisubstituted benzene.

Accordingly, by using the adsorbent of the present invention, it is possible to selectively and efficiently separate 2,6-DCT in high purity.

The mixture of DCT isomers to be treated by the present invention may be a mixture of DCT isomers obtained by chlorination of toluene and comprising 2,3-DCT (from 8 to 12%), 2,4-DCT (from 20 to 35%), 2,5-DCT (from 25 to 55%), 2,6-DCT (from 5 to 25%) and 3,4-DCT (from 5 to 12%), or a mixture of DCT isomers obtained by chlorination of o-chlorotoluene and comprising 2,3-DCT (from 5 to 20%), 2,4-DCT (from 10 to 25%), 2,5-DCT (from 30 to 70%) and 2,6-DCT (from 5 to 30%).

Preferably, the above-mentioned mixture of DCT isomers is further preliminarily rectified into a fraction having a boiling point of about 201° C. and comprising 2,4-DCT, 2,5-DCT and 2,6-DCT and a fraction having a boiling point of from about 208° to 209° C. and comprising 2,3-DCT and/or 3,4-DCT and the method of the present invention is particularly effective for the separation and recovery of 2,6-DCT from the former fraction of the mixture of DCT isomers.

ZSM-5 type zeolite to be used in the present invention is a high silica type zeolite represented by the following general formula and is a zeolite belonging to a Pentasil group. The crystal structure is a rhombic system belonging to a Pnma space group, wherein the lattice constants are a=20.1 Å, b=19.9 Å and c=13.4 Å.

The sodium ions in the general formula are readily exchangeable by other cations as is well known to those skilled in the art having a common knowledge relating to the production of zeolite.

As the cation component, any component may substantially be used. However, it is preferably at least one cation selected from the group consisting of monovalent or bivalent metals, protons or ammonium ions. Particularly preferred are protons.

For the ion exchange with these cations, it is usually preferred to contact to the zeolite an aqueous solution of a nitrate of at least one type of such cations, as an ion exchange treating solution, for ion exchange. Instead of the nitrate, other soluble salts such as a chloride may likewise preferably be employed in the form of an aqueous solution. Such cations may be applied by a single operation of ion exchange treatment with the ion exchange solution, or such a treatment may be conducted in a plurality of separate operations. The treatment may be conducted in a batch system or in a continuous system. The temperature for this treatment is usually within a range of from 20° to 100° C., but is preferably from 50° to 100° C. to facilitate the ion exchange rate. After the ion exchange treatment, it is necessary to adequately wash the zeolite with water until e.g. $NO_3^-$ or $Cl^-$ ions are no longer detected.

Further, prior to the use of the zeolite as a catalyst, it is necessary to preliminarily remove the zeolitic water. Usually, the content of the zeolitic water can be reduced at a temperature of 100° C. or higher. Preferably, the zeolitic water is almost completely removed by heating at a temperature of from 300° to 600° C.

The zeolite to be used in the present invention may be in the form of a powder, crushed pieces, or molded products obtained by a molding method such as compression molding or extrusion molding. If necessary, a binder such as alumina sol or clay may be added at the time of the molding. In a small scale operation, the zeolite may be used in a powder form. For the industrial purpose, it is preferred to employ spherical molded products having a diameter of from 0.1 to 10 mm to avoid pressure loss. The selection of the shape may suitably be made depending upon the particular apparatus to be employed.

The ratio of $SiO_2/Al_2O_3$ is not critical, but it is preferably within a range of from 10 to 50.

The process for the preparation of ZSM-5 and its composition are disclosed in Japanese Examined Patent Publication No. 10064/1971, and its crystal structure is described in detail in "Nature" vol 271, No. 30, March issue, p 437 (1978). Namely, ZSM-5 can be produced by using an organic amine, and its crystal structure has characteristic pores with a ten-membered ring of oxygen.

The method of the present invention may be conducted by a batch method or a continuous method by means of a fixed bed system, known per se as a separation technique.

The separation technique of the present invention is conducted basically in a cycle of the steps of adsorption, washing, desorption and regeneration of the adsorbent by using one or more chambers for adsorption packed with the adsorbent.

Namely, a mixture of DCT isomers containing 2,6-DCT as the substance to be separated and at least one of DCT isomers other than 2,3-DCT, is contacted to a ZSM-5 type adsorbent in the chamber for adsorption, whereby the desired 2,6-DCT is selectively separated as a non-adsorbed component while other components are strongly adsorbed.

The separation by adsorption according to the present invention is conducted usually at a temperature within a range of from room temperature to about 300° C., preferably from 150° to 250° C. If the temperature is higher than 300° C., a side reaction such as a disproportionation reaction of DCT is likely to take place, such being undesirable.

The pressure for the separation reaction is usually from the atmospheric pressure to about 50 kg/cm$^2$, preferably from the atmospheric pressure to about 30 kg/cm$^2$. If the pressure is higher than about 50 kg/cm$^2$, the operation will be costly.

Further, a substance which does not adversely affect the adsorption-desorption during the separation reaction, may be added as a diluent to the mixture of DCT isomers. Usually, however, such an addition is not desirable from the viewpoint of the efficiency of apparatus.

There is no particular restriction as to the method for desorbing the strongly adsorbed DCT isomers after the operation for adsorption. There may be employed various methods such as (1) desorption by a temperature difference, (2) desorption by a pressure difference, (3) desorption by an inert gas, (4) desorption by steam or (5) desorption by substitution by a third component, or a combination of these methods.

The separating ability by the adsorption of the DCT isomers mixture by ZSM-5 type zeolite used in the method of the present invention, is such that when a mixture comprising, for instance, 2,4-DCT, 2,5-DCT and 2,6-DCT is subjected to the separation by adsorption with ZSM-5, 2,4-DCT and 2,5-DCT will be adsorbed, while desired 2,6-DCT will be separated without being adsorbed. Namely, ZSM-5 has an extremely large adsorbing capacity for 2,4-DCT and 2,5-DCT, and the concentration of 2,6-DCT in a non-adsorbed effluent changes ideally as shown by the break through curve in FIG. 1. Accordingly, the separating ability of ZSM-5 for adsorption can be represented by the amount (% by weight) of the 2,6-DCT effluent obtained up to the break through point per 1 g of the zeolite.

$$\text{2,6-DCT separating ability(wt. \%)} = \frac{A(g) \times B(\text{wt. \%})}{\text{Amount of ZSM-5(g)}}$$

A: Total amount (g) of the effluent up to the break through point

B: Average concentration (wt. %) of 2,6-DCT in the effluent

The higher the 2,6-DCT separating ability, the more advantageous from the industrial point of view in that 2,6-DCT of a high purity can thereby efficiently be obtained.

Thus, according to the method of the present invention, it is possible, by the adsorption and separation of the mixture of DCT isomers by means of ZSM-5 type zeolite, not only to selectively obtain 2,6-DCT of a high purity which used to be difficult to achieve, but also to effectively utilize other DCT isomers separated as the strongly adsorbed components since they can be subjected to an isomerization reaction, followed by separation treatment for adsorption again. Further, ZSM-5 can be re-used for a long period of time. Thus, the industrial contribution of the method of the present invention is very high.

Now, the present invention will be described in detail with reference to the Examples. However, it should be understood that the present invention is by no means restricted by these specific Examples.

REFERENCE EXAMPLE 1

A powder of ZSM-5 type zeolite comprising 90.1% by weight of $SiO_2$, 6.1% by weight of $Al_2O_3$ and 3.8% by weight of $Na_2O$ with a $SiO_2/Al_2O_3$ ratio of 25.1, was prepared in accordance with the process of Example 1 of Japanese Examined Patent Publication No. 10064/1971. Then, the zeolite powder was subjected to ion exchange treatment five times by using an aqueous solution containing 10% by weight of ammonium nitrate (solid-liquid ratio: 2.0 liter/kg, 95° C.), thoroughly washed with water, dried at 150° C. for 5 hours, and then calcined at 500° C. for 3 hours to obtain a H-ZSM-5 type zeolite powder. From the X-ray analysis, this H-ZSM-5 type zeolite was found to be the same as the H-ZSM-5 manufactured by Mobil Oil Corp.

REFERENCE EXAMPLE 2

In the same manner as in Reference Example 1, a ZSM-5 type zeolite powder comprising 93.6% by weight of $SiO_2$, 3.2% by weight of $Al_2O_3$ and 3.2% by weight of $Na_2O$ with a $SiO_2/Al_2O_3$ ratio of 49.6, was obtained. This zeolite powder was treated in the same manner as in Reference Example 1 to obtain a H-ZSM-5 type zeolite powder.

EXAMPLE 1

8.43 g of the H-ZSM-5 type zeolite powder of Reference Example 1 was packed in a metal column having an inner diameter of 9.8 mm and a length of 16.3 cm, and a mixture of DCT isomers was introduced at a rate of 0.1 ml/min under a nitrogen pressure of 2 kg/cm$^2$ at 200° C. The mixture of DCT isomers introduced, had a composition of 2,4-DCT/2,5-DCT/2,6-DCT=24/44/32 by weight ratio.

The composition of the non-adsorbed effluent from the outlet of the column, was analyzed by gas chromatography, whereby it was found that the initial concentration of 2,6-DCT was 100%, and the 2,6-DCT concentration gradually decreased and upon expiration of 10 minutes, reached the break through point where the composition of the non-adsorbed effluent was the same as the feed liquid.

The total amount of the non-adsorbed effluent up to the break through point was 0.71 g.

The average DCT composition of the total effluent was 2,4-DCT/2,5-DCT/2,6-DCT=7.1/13.4/79.5 by weight ratio.

Thus, the 2,6-DCT separating ability was 6.70% by weight.

COMPARATIVE EXAMPLES 1 to 4

The adsorption operation was conducted in the same manner by using the same apparatus with respect to a mixture of DCT isomers having the same composition as in Example 1 except that the type of zeolite was changed.

The zeolite used was a Na-X type (Molecular Sieve 13X, manufactured by Union Showa K.K.), a K-Y type (TSZ-320 KOA, manufactured by Toyo Soda Manufacturing Co., Ltd.), a Na-A type (Molecular Sieve 4A, manufactured by Union Showa K.K.) or a K-L type (TSZ-500 KOA, manufactured by Toyo Soda Manufacturing Co., Ltd.). 10 g of such a zeolite was packed in the metal column. The average DCT composition of the non-adsorbed effluent obtained up to the break through point is shown in Table 1.

TABLE 1

| Comparative Example No. | Type of zeolite | Composition of effluent (wt. %) | | | Amount of effluent (g) |
|---|---|---|---|---|---|
| | | 2,4-DCT | 2,5-DCT | 2,6-DCT | |
| 1 | Na-X | 30.9 | 43.5 | 25.6 | 1.4 |
| 2 | K-Y | 13.4 | 37.3 | 49.3 | 1.4 No adsorptive or separating effect |
| 3 | Na-A | 24.0 | 44.0 | 32.0 | |
| 4 | K-L | 24.0 | 44.0 | 32.0 | No adsorptive or separating effect |

EXAMPLES 2 to 5

The adsorption operation was conducted in the same manner by using the same apparatus as in Example 1 except that the cation of H-ZSM-5 type zeolite of Reference Example 1 was changed to calcium, magnesium, copper and sodium, respectively, whereby the 2,6-DCT separating ability was measured. The results are shown in Table 2.

TABLE 2

| Example No. | Type of cation | 2,6-DCT separating ability |
|---|---|---|
| 2 | Ca | 5.21 wt. % |
| 3 | Mg | 2.73 wt. % |
| 4 | Cu | 4.82 wt. % |
| 5 | Na | 4.67 wt. % |

The cation exchange was conducted by treating the H-ZSM-5 type zeolite with an aqueous solution containing from 5 to 10% by weight of a nitrate in the same manner as in Reference Example 1.

EXAMPLES 6 and 7

The adsorption operation was conducted in the same manner by using the same apparatus as in Example 1 except that the temperature for adsorption was changed, whereby the 2,6-DCT separating ability was measured. The results are shown in Table 3. In the case where the temperature for adsorption was 300° C., a disproportionation reaction took place, and the production of o-chlorotoluene and toluene as by-products was observed.

TABLE 3

| Example No. | Temp. for adsorption | Composition of total effluent up to the break through point | | | | | 2,6-DCT separating ability |
|---|---|---|---|---|---|---|---|
| | | 2,4-DCT | 2,5-DCT | 2,6-DCT | o-chlorotoluene | Toluene | |
| 6 | 250° C. | 7.4 | 13.5 | 79.1 | 0 | 0 | 6.47 wt. % |
| 7 | 300° C. | 7.1 | 12.9 | 75.6 | 4.2 | 0.1 | 6.10 wt. % |

EXAMPLES 8 to 10

The adsorption operation was conducted in the same manner by using the same apparatus as in Example 1 except that the feed liquid mixture of DCT isomers was changed. The composition of the feed liquid and the average composition of the non-adsorbed effluent up to the break through point, are shown in Table 4.

TABLE 4

| Example No. | Composition of feed liquid (wt. %) | | | | | Composition of effluent (wt. %) | | | | |
|---|---|---|---|---|---|---|---|---|---|---|
| | 2,3-DCT | 2,4-DCT | 2,5-DCT | 2,6-DCT | 3,4-DCT | 2,3-DCT | 2,4-DCT | 2,5-DCT | 2,6-DCT | 3,4-DCT |
| 8 | — | 40.2 | 36.4 | 23.4 | — | — | 8.5 | 12.9 | 78.6 | — |
| 9 | 14.7 | 22.8 | 32.9 | 29.6 | — | 28.1 | 7.6 | 13.5 | 50.8 | — |
| 10 | 20.1 | 14.5 | 25.4 | 20.4 | 19.6 | 33.5 | 6.4 | 11.1 | 43.1 | 5.9 |

EXAMPLE 11

The same operation as in Example 1 was conducted except that 7.85 g of the H-ZSM-5 type zeolite of Reference Example 2 was employed. The following results were obtained.

The total amount of the non-adsorbed effluent up to the break through point: 0.7 g The average DCT composition of this total effluent was 2,4-DCT/2,5-DCT/2,6-DCT=9.9/20.4/69.7 by weight ratio.

Thus, the 2,6-DCT separating ability was 6.22% by weight.

EXAMPLE 12

The same operation as in Example 1 was conducted except that 11.24 g of silicalite (JE-15, manufactured by Union Showa K.K.) which is regarded as ZSM-5 type zeolite containing no substantial aluminum component. The following results were obtained.

The total amount of the non-adsorbed effluent up to the break through point: 1.75 g.

The average DCT composition of this total effluent was 2,4-DCT/2,5-DCT/2,6-DCT=18.5/35.5/46.0 by weight ratio.

Thus, the 2,6-DCT separating ability was 7.16% by weight.

We claim:

1. A method for selective separation of 2,6-dichlorotoluene from a mixture of dichlorotoluene isomers by means of a zeolite-type adsorbent, wherein ZSM-5 type zeolite is used as the adsorbent for selectively separating 2,6-dichlorotoluene as a non-adsorbed component.

2. The method according to claim 1, wherein the separation is conducted at a temperature of from room temperature to 300° C.

3. The method according to claim 1, wherein the separation is conducted under a pressure of from the atmospheric pressure to about 50 kg/cm$^2$.

* * * * *